US00PP17535P2

(12) United States Plant Patent
Wain

(10) Patent No.: US PP17,535 P2
(45) Date of Patent: Mar. 27, 2007

(54) ***CHRYSANTHEMUM* PLANT NAMED 'YODIANA'**

(50) Latin Name: *Chrysanthemum×morifolium*
Varietal Denomination: Yodiana

(75) Inventor: Peter Wain, Southampton (GB)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/212,388

(22) Filed: Aug. 26, 2005

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Yodiana', characterized by its compact, upright and somewhat outwardly spreading plant habit; freely branching habit; dense and full plant habit; uniform and freely flowering habit; medium-sized decorative-type inflorescences with elongated oblong-shaped ray florets; yellow-colored ray florets; and natural season flowering in early September in the Northern Hemisphere.

2 Drawing Sheets

Botanical designation: *Chrysanthemum×morifolium.*
Cultivar denomination: 'Yodiana'.

BACKGROUND OF THE INVENTION

The present invention relates to a new and distinct cultivar of *Chrysanthemum* plant, botanically known as *Chrysanthemum×morifolium,* commercially known as a garden-type *Chrysanthemum* and hereinafter referred to by the name 'Yodiana'.

The new cultivar is a product of a planned breeding program conducted by the Inventor in Fareham, Hants, United Kingdom. The objective of the breeding program is to create new garden-type *Chrysanthemum* cultivars having inflorescences with desirable inflorescence forms, attractive floret colors and good garden performance.

The new *Chrysanthemum* originated from a cross-pollination made in March, 2002 in Fareham, Hants, United Kingdom, of a proprietary selection of *Chrysanthemum× morifolium* identified as code number G207-7, not patented, as the female, or seed, parent with the *Chrysanthemum× morifolium* cultivar Brangold, not patented, as the male, or pollen, parent. The new *Chrysanthemum* was discovered and selected by the Inventor as a single flowering plant within the progeny of the stated cross-pollination grown in a controlled environment in Fareham, Hants, United Kingdom in September, 2002. The selection of this plant was based on its desirable inflorescence form, attractive floret coloration and good garden performance.

Asexual reproduction of the new cultivar by terminal vegetative cuttings in a controlled environment in Fareham, Hants, United Kingdom since December, 2002, has shown that the unique features of this new *Chrysanthemum* are stable and reproduced true to type in successive generations.

SUMMARY OF THE INVENTION

The cultivar Yodiana has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yodiana'. These characteristics in combination distinguish 'Yodiana' as a new and distinct cultivar:

1. Upright, somewhat outwardly spreading and rounded plant habit.
2. Freely branching habit; dense and full plants.
3. Uniform and freely flowering habit.
4. Medium-sized decorative-type inflorescences with elongated oblong-shaped ray florets.
5. Yellow-colored ray florets.
6. Natural season flowering in early September in the Northern Hemisphere.

In side-by-side comparisons conducted in Alva, Fla., plants of the new *Chrysanthemum* differed from plants of the female parent selection in the following characteristics:

1. Plants of the new *Chrysanthemum* were more rounded than plants of the female parent selection.
2. Plants of the new *Chrysanthemum* had smaller inflorescences than plants of the female parent selection.
3. Inflorescences of plants of the new *Chrysanthemum* had fewer disc florets than inflorescences of plants of the female parent selection.
4. Plants of the new *Chrysanthemum* and the female parent selection differed in ray floret coloration as plants of the female parent selection had white-colored ray florets.
5. Plants of the new *Chrysanthemum* flowered about one week earlier than plants of the female parent selection when grown under natural season conditions.

In side-by-side comparisons conducted in Alva, Fla., plants of the new *Chrysanthemum* differed from plants of the male parent, the cultivar Brangold, in the following characteristics:

1. Plants of the new *Chrysanthemum* had darker green-colored leaves than plants of the cultivar Brangold.
2. Plants of the new *Chrysanthemum* had smaller inflorescences than plants of the cultivar Brangold.
3. Inflorescences of plants of the new *Chrysanthemum* had fewer disc florets than inflorescences of plants of the cultivar Brangold.
4. Ray florets of the new *Chrysanthemum* were darker yellow in color than ray florets of plants of the cultivar Brangold.
5. Plants of the new *Chrysanthemum* flowered about two days earlier than plants of the cultivar Brangold when grown under natural season conditions.
6. Inflorescences of plants of the new *Chrysanthemum* were longer lasting than inflorescences of plants of the cultivar Brangold.

Plants of the new *Chrysanthemum* can be compared to plants of the *Chrysanthemum* cultivar Jessica, disclosed in U.S. Plant Pat. No. 7,587. In side-by-side comparisons conducted in Alva, Fla., plants of the new *Chrysanthemum* differed from plants of the cultivar Jessica in the following characteristics:

1. Plants of the new *Chrysanthemum* were more rounded than plants of the cultivar Jessica.
2. Plants of the new *Chrysanthemum* had smaller inflorescences than plants of the cultivar Jessica.
3. Plants of the new *Chrysanthemum* had more disc florets per inflorescence than plants of the cultivar Jessica.
4. Plants of the new *Chrysanthemum* flowered more uniformly than plants of the cultivar Jessica.

Plants of the new *Chrysanthemum* can also be compared to plants of the *Chrysanthemum* cultivar Gold Crest, disclosed in U.S. Plant Pat. No. 11,606. In side-by-side comparisons conducted in Alva, Fla., plants of the new *Chrysanthemum* differed from plants of the cultivar Gold Crest in the following characteristics:

1. Plants of the new *Chrysanthemum* were more rounded than plants of the cultivar Gold Crest.
2. Plants of the new *Chrysanthemum* flowered more freely and more uniformly than plants of the cultivar Gold Crest.
3. Plants of the new *Chrysanthemum* had smaller inflorescences than plants of the cultivar Gold Crest.
4. Plants of the new *Chrysanthemum* had more disc florets per inflorescence than plants of the cultivar Gold Crest.
5. Plants of the new *Chrysanthemum* flowered about three to four days earlier than plants of the cultivar Gold Crest when grown under natural season conditions.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Yodiana' grown in a container.

The photograph on the second sheet comprises a close-up view of typical inflorescences of the cultivar 'Yodiana'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the summer in a glass-covered greenhouse and under conditions and practices which approximate those generally used in commercial garden-type *Chrysanthemum* production. Rooted cuttings were planted in 15.25-cm containers, grown under artificial long day conditions (four-hour night interruption) and pinched about ten days later. About ten days after the pinch, plants were then exposed to artificial short day conditions (11.5 hours light) until flowering. During the production of the plants, temperatures ranged from 18° C. to 38° C. Measurements and numerical values represent averages for typical flowering plants.

Botanical classification: *Chrysanthemum×morifolium* cultivar Yodiana.

Commercial classification: Decorative-type garden *Chrysanthemum.*

Parentage:

*Female, or seed, parent.*—Proprietary selection of *Chrysanthemum×morifolium* identified as code number G207-7, not patented.

*Male, or pollen, parent.*—*Chrysanthemum×morifolium* cultivar Brangold, not patented.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum.* Inverted triangle with mounded crown. Stems initially upright, then somewhat outwardly spreading; rounded growth habit. Freely branching with about nine primary branches with secondary lateral branches potentially forming at every node. Moderately vigorous to vigorous.

*Plant height.*—About 26 cm.

*Plant diameter.*—About 36.5 cm.

*Lateral branches.*—Length: About 24 cm. Diameter: About 4 mm. Internode length: About 1.2 cm. Aspect: Upright and somewhat outwardly spreading. Texture: Pubescent. Color: Close to 146A.

*Foliage description.*—Leaf arrangement: Alternate. Length: About 4.6 cm. Width: About 3.2 cm. Apex: Cuspidate. Base: Mostly truncate with attenuate tendencies. Margin: Palmately lobed, sinuses parallel to divergent. Texture, upper surface: Slightly pubescent. Texture, lower surface: Pubescent; veins prominent. Color: Developing and fully expanded foliage, upper surface: More green than 147A. Developing and fully expanded foliage, lower surface: Close to 147B. Venation, upper surface: More green than 147A. Venation, lower surface: Close to 147B. Petiole length: About 1.7 cm. Petiole diameter: About 2 mm. Petiole color, upper surface: Close to 146A. Petiole color, lower surface: Close to 146B.

Inflorescence description:

*Appearance.*—Decorative-type inflorescence form with elongated oblong-shaped ray florets. Inflorescences borne on terminals above foliage, arising from leaf axils. Ray florets developing acropetally on a capitulum. About seven inflorescences per secondary lateral branch.

*Flowering response.*—Under natural season conditions, plants flower in early September in the Northern Hemisphere.

*Inflorescence bud* (*before showing color*).—Height: About 4 mm. Diameter: About 5 mm. Shape: Oblate. Color (lower surface of phyllaries): More green than 147A.

*Inflorescence size.*—Diameter: About 3 cm. Depth (height): About 1.1 cm. Disc diameter: About 4 mm. Receptacle diameter: About 4 mm.

*Ray florets.*—Shape: Elongated oblong-shaped. Length: About 1.4 cm. Width: About 5 mm. Corolla tube length: About 3 mm. Corolla tube diameter: About 1 mm. Apex: Mostly emarginate. Margin: Fused. Texture, upper and lower surfaces: Smooth, glabrous; satiny. Orientation: Initially upright, eventually perpendicular to the peduncle. Number of ray florets per inflorescence: About 145 in numerous whorls. Color: When opening and fully opened, upper surface: Close to 6A to 6B. When opening and fully opened, lower surface: Close to 6C to 6D.

*Disc florets.*—Shape: Tubular, elongated. Length: About 4 mm. Width, apex: About 1 mm. Width, base: About 1 mm. Number of disc florets per inflorescence: About 48. Color: Immature: Close to 9A. Mature: Apex: Close to 9A. Mid-section: Close to 154D. Base: Close to 155D.

*Phyllaries.*—Quantity per inflorescence: About 20. Length: About 5 mm. Width: About 2 mm. Shape: Ligulate. Apex: Acute. Base: Truncate. Margin: Entire. Texture, upper surface: Smooth, waxy. Texture, lower surface: Pubescent. Color, upper surface: Close to 146A. Color, lower surface: More green than 147A.

*Peduncle.*—Length: First peduncle: About 1.75 cm. Fourth peduncle: About 2.5 cm. Diameter: About 1.5 mm. Strength: Strong. Aspect: About 45° from vertical. Texture: Pubescent. Color: Close to 146A.

*Reproductive organs.*—Androecium: Present on disc florets only. Anther length: Less than 1 mm. Anther color: Close to 12A. Amount of pollen: None observed. Gynoecium: Present on both ray and disc florets. Style length: About 5 mm. Style color: Close to 154A. Stigma color: Close to 9A.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0° C. to more than 38° C.

It is claimed:

1. A new and distinct cultivar of *Chrysanthemum* plant named 'Yodiana', as illustrated and described.

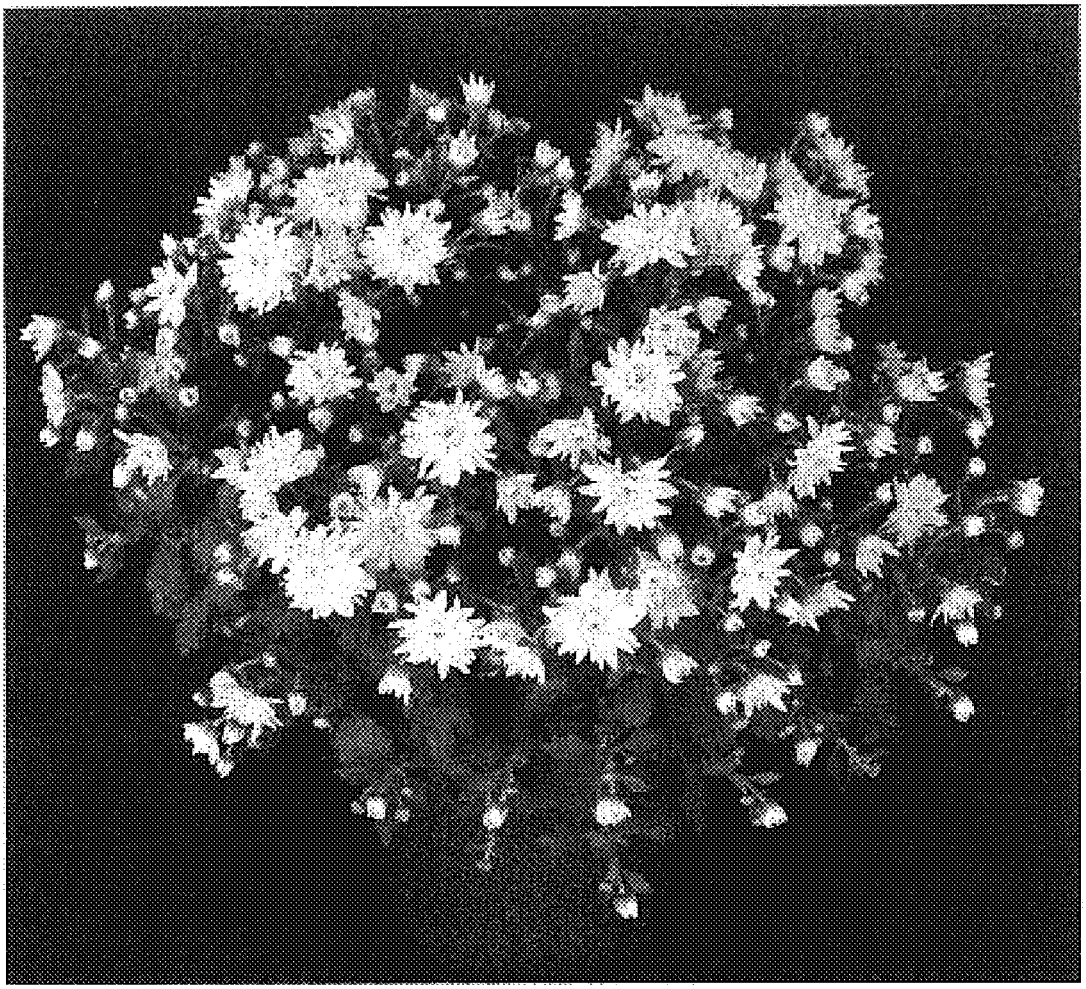

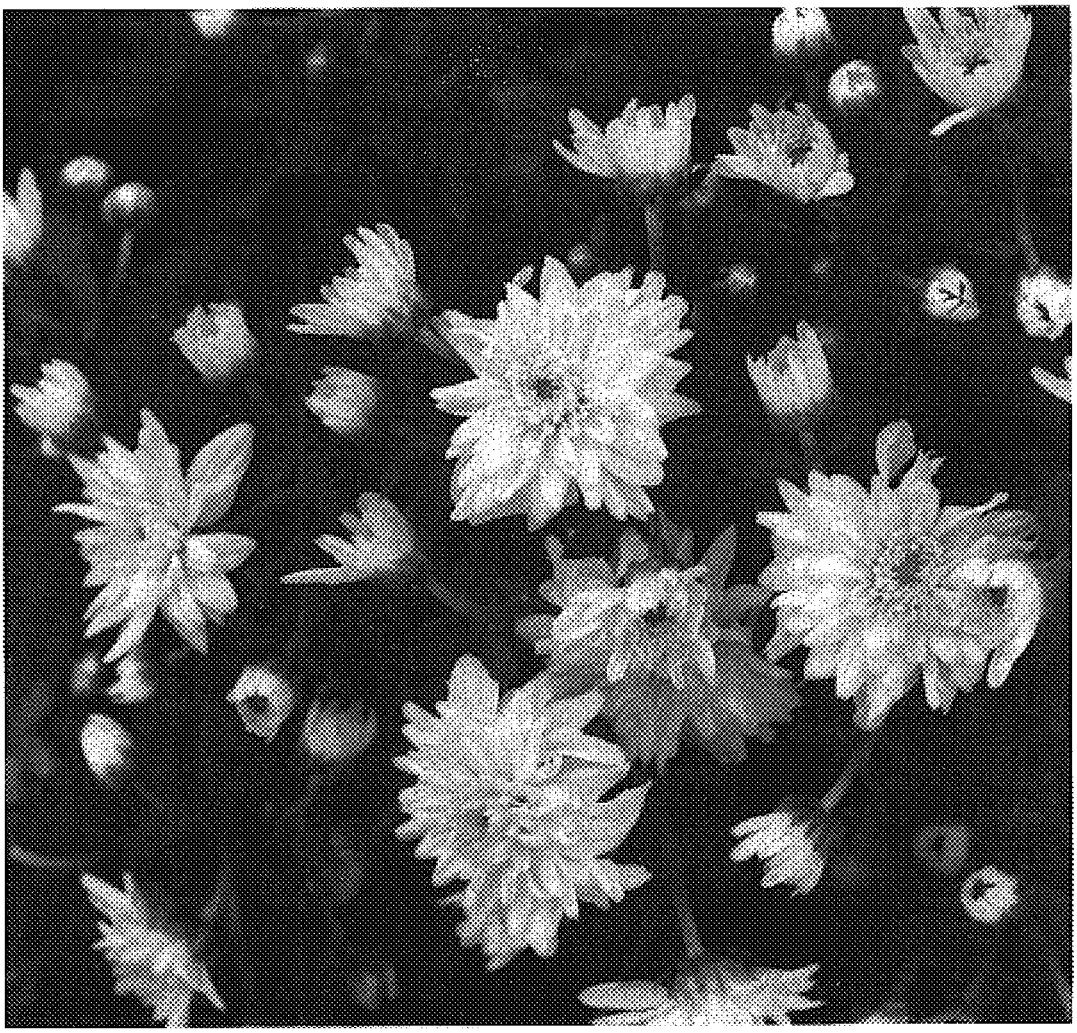

* * * * *